(12) United States Patent
Karling et al.

(10) Patent No.: US 8,573,220 B2
(45) Date of Patent: Nov. 5, 2013

(54) DEVICE AND METHOD FOR TRACHEOTOMY

(75) Inventors: Jonas Karling, Nacka (SE); Gregory Margolin, Stockholm (SE)

(73) Assignee: Safetrach AB, Nacka (SE)

( * ) Notice: Subject to any disclaimer, the term of this patent is extended or adjusted under 35 U.S.C. 154(b) by 1042 days.

(21) Appl. No.: 11/997,822

(22) PCT Filed: Aug. 9, 2006

(86) PCT No.: PCT/SE2006/050279
§ 371 (c)(1),
(2), (4) Date: Jul. 7, 2008

(87) PCT Pub. No.: WO2007/018472
PCT Pub. Date: Feb. 15, 2007

(65) Prior Publication Data
US 2008/0295848 A1     Dec. 4, 2008

(30) Foreign Application Priority Data
Aug. 9, 2005 (SE) ....................................... 0501786

(51) Int. Cl.
*A61M 16/00* (2006.01)
(52) U.S. Cl.
USPC ................................. 128/207.29; 128/207.14
(58) Field of Classification Search
USPC ............ 128/204.18, 207.14, 207.15, 207.29;
600/116, 117, 272, 514; 604/185, 190,
604/200, 214, 237; 606/108, 167, 170, 172,
606/181, 184, 185
See application file for complete search history.

(56) References Cited

U.S. PATENT DOCUMENTS

| 2,583,892 | A | * | 1/1952 | Shellhouse ................... 606/137 |
| 4,232,405 | A | * | 11/1980 | Janovsky ......................... 623/60 |
| 4,444,185 | A | * | 4/1984 | Shugar ..................... 128/207.29 |
| 4,577,986 | A | * | 3/1986 | Wang ............................... 403/93 |

(Continued)

FOREIGN PATENT DOCUMENTS

| DE | 10 2004 026 316 |   | 6/2005 |
| GB |    2273875 | A * | 7/1994 |

OTHER PUBLICATIONS

User Manuel for COOK Critical Care Inc., Bloomington Indiana. 2000.

(Continued)

*Primary Examiner* — Lynne Anderson
*Assistant Examiner* — Kathryn E Ditmer
(74) *Attorney, Agent, or Firm* — Merchant & Gould P.C.

(57) ABSTRACT

A device (11) for facilitating tracheotomy. The device comprises a first branch (92), which is adapted to be introduced down the trachea of a patient, such that the end thereof is located below the larynx, and a second branch (114), adapted to be arranged on the outside of the neck with the end thereof located adjacent to the site intended for the tracheostoma. The end of the second branch comprises a guiding tube for a needle, and the end of the first branch comprises a protection plate. When the needle is moved towards the skin through the guiding tube and penetrates the skin and tracheal wall in order to provide said tracheostoma, the needle is directed towards the protection plate, and may engage it after passage through the tracheal wall. In such a manner the other side of the tracheal wall is protected. Furthermore, the tracheostoma will automatically be located at the best position.

27 Claims, 8 Drawing Sheets

(56) References Cited

U.S. PATENT DOCUMENTS

| | | | | |
|---|---|---|---|---|
| 4,713,053 A | * | 12/1987 | Lee | 604/542 |
| 5,071,428 A | * | 12/1991 | Chin et al. | 606/184 |
| 5,234,434 A | * | 8/1993 | Goble et al. | 606/96 |
| 5,265,969 A | * | 11/1993 | Chuang | 403/94 |
| 5,330,468 A | * | 7/1994 | Burkhart | 606/96 |
| 5,387,223 A | * | 2/1995 | Agee et al. | 606/186 |
| 5,709,400 A | * | 1/1998 | Bonnier et al. | 280/650 |
| 5,728,072 A | * | 3/1998 | Hastings | 606/185 |
| 5,893,864 A | * | 4/1999 | Brakey | 606/181 |
| 6,217,605 B1 | * | 4/2001 | Kondo et al. | 607/88 |
| 6,575,158 B1 | * | 6/2003 | Chelly et al. | 128/200.26 |
| 6,596,001 B2 | * | 7/2003 | Stormby et al. | 606/144 |
| 6,613,039 B1 | * | 9/2003 | Namba | 604/541 |
| 7,124,509 B1 | * | 10/2006 | Hawk | 30/160 |
| 7,938,810 B2 | * | 5/2011 | Spranza et al. | 604/264 |
| 2002/0066450 A1 | * | 6/2002 | Bonutti | 128/200.26 |
| 2003/0136414 A1 | * | 7/2003 | Turnbull | 128/207.29 |
| 2004/0092891 A1 | * | 5/2004 | Spranza et al. | 604/264 |
| 2004/0098003 A1 | * | 5/2004 | Nishiki | 606/167 |
| 2004/0103900 A1 | | 6/2004 | Melker et al. | |

OTHER PUBLICATIONS

PDF CD-ROM presentation materials for COOK Critical Care Inc., Bloomington Indiana. 2000.

* cited by examiner

DEVICE AND METHOD FOR TRACHEOTOMY

FIELD OF THE INVENTION

The present invention pertains to the field of tracheotomy, i.e. creation of an opening in the windpipe (trachea) just below the larynx towards the surrounding air.

BACKGROUND OF THE INVENTION

Tracheotomy is one of the most common life saving operations that is done within medical care. A tracheotomy involves opening a hole in the neck part of the trachea. The term tracheostomy is sometimes used interchangeably with tracheotomy. Strictly speaking, however, tracheostomy usually refers to the opening itself while a tracheotomy is the actual operation.

Some common indications for a tracheotomy are:
Respiratory obstruction—an obstruction of the upper respiratory passages;
Respiratory failure/respiratory insufficiency;
Respiratory paralysis;
Removal of retained secretion;
Reduction of dead space.

About 15% of all patients treated in intensive care units need a tracheotomy.

Tracheotomy was already performed in ancient times. Of course, the procedure was at that time associated with high risk and was consequently rarely performed up to the beginning of the twentieth century. At that time Chevalier Jackson described routines for performing the procedure, which lead to making the procedure safer and even more common. He described what is called open tracheotomy.

Open tracheotomy is a surgical operation that is performed in an operating theatre by a surgical team that consists of an ear, nose and throat surgeon, and preferably an assisting surgeon, as well as a theatre nurse, an anesthesiologist, and an anesthesia nurse and also a nurse's assistant. A sterile sheet environment is necessary. It is preferred to perform the operation on an intubated patient in anesthesia together with supplementary local anesthesia in the surgical area. During acute situations, when intubation is difficult or impossible to be done, the surgical operation is performed with the patient awake, in local anesthesia. A horizontal incision is made in the skin above the breastbone (above the suprastenal notch). Then, a cut is performed sharply through the platysma. The straight neck muscles are pulled aside. However, the thyroid gland isthmus should preferably be avoided, but if it is in the way, it is split and bound up. The trachea is then opened with a horizontal incision for adults and with a vertical incision for children. A tracheal tube is inserted and connected to a respirator. Then the wound is closed with sparse sutures and finally the tube is fixed with sutures and tracheal bands.

During the last thirty years even so called percutaneous tracheotomy has been established. This technique became widely spread despite highly frequent complications. The frequency of complications could be reduced considerably by introducing an endoscopical guidance. The result of this development was that the indications for a tracheotomy changed and specialists who perform a tracheotomy, who earlier exclusively were ear, nose and throat specialist, include now even intensive care physicians.

Furthermore, percutaneous tracheotomy was already described during the sixties, but was not accepted as a secure surgical operation before the eighties when the group of Ciaglia introduced dilatators. The surgical operation may be performed bedside on an intensive care unit in anesthesia by two trained physicians, whereof one carries out the surgical operation and the other inspects the trachea from the inside by means of a bronchoscope. Moreover, an anesthesia nurse is necessary.

The surgical area is locally anesthetized and a horizontal incision is made in the skin. A cuffed endotracheal tube is pulled up against the vocal cords. The tracheal wall is, under inspection via a bronchoscope, punctured with a needle through the endotracheal tube. Subsequently a guidewire is introduced. On the latter a dilatator having increasing gauge is then introduced. Finally, a tracheal tube, which is slipped on a dilatator, is introduced into the tracheostoma that is produced. The dilatator is withdrawn and the tracheal tube is positioned. The method does not leave any wounds that have to be sutured, and the tracheal tube is fixed in the same manner as with open technique. The patient's head must be kept centered, such that the puncture does not end up aside of the trachea. The position of the percutaneous tracheotomy is also located 2 cm above the breastbone.

The surgical operation necessitates staff that is acquainted with this technique. A number of surgical operations under experienced supervision are necessary before it can be performed independently. The frequency of complications is rather high and comprises amongst others pneumothorax, perforation of the rear tracheal wall and oesophagus, as well as bleedings. The procedure is complicated with patients who have a short and thick neck, and patients having enlarged thyroid gland. It is not recommended for children.

The percutaneous technique has eliminated drawbacks that an open tracheotomy involves, including the need of an operation theatre and staff intensive effort, and that it leaves an open wound that can become an infection site. Furthermore, it also puts heavy demands on surgical skill training. Moreover, the open technique is burdened with the risk of surgical complications.

Hence, there is a need for an improved tracheotomy technique. In particular a device and method allowing for increased flexibility, cost-effectiveness, as well as patient safety and comfort would be advantageous.

SUMMARY OF THE INVENTION

Accordingly, the present invention preferably seeks to mitigate, alleviate or eliminate, amongst others, one or more of the above-identified, or other, deficiencies and disadvantages in the art, singly or in any combination, and solves for instance the above mentioned problems at least partly by providing a device and a method according to the appended patent claims.

According to one aspect of the invention, a device is provided. The device for facilitating tracheotomy comprises a first branch, adapted to be introduced into the trachea of a patient, such that the distal end thereof is located below the larynx, and a second branch, adapted to be arranged at the outside of the neck with the distal end thereof located adjacent to a site that is intended for a tracheostoma, wherein the end of one of the branches comprises a guide for a sharp object, and the end of the other branch comprises a receiving means, and wherein the first branch and the second branch are joined to each other in such a manner that the guide is directed towards the receiving means, whereby, when the sharp object penetrates the skin and the tracheal wall in order to carry out the tracheostoma, the sharp object is directed towards the receiving means.

According to another aspect of the invention, a method is provided. The method of carrying out a tracheotomy comprises introducing a first branch of a device for facilitating tracheotomy down a trachea of a patient, such that the distal end thereof is located below the larynx, and arranging a second branch of the device on the outside of the neck with the distal end thereof located adjacent to the site that is intended for a tracheostoma, wherein the distal end of one of the first and second branches comprises a guide for a sharp object, receiving means, and wherein the first and second branch are joined to each other in such a manner that the guide is directed towards the receiving means, as well as penetrating the skin and tracheal wall with said sharp object in order to carry out the tracheotomy by directing the sharp object towards the receiving means through said guiding device.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION OF EMBODIMENTS OF THE INVENTION

Figure 1:
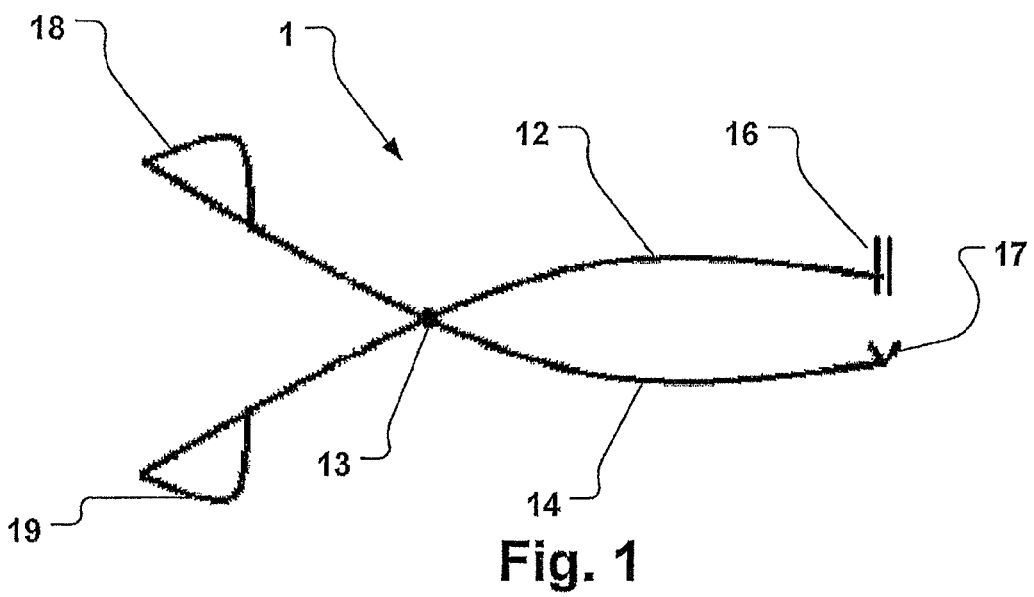
FIG. 1 is a schematic illustration of a device that is configured to be used during creation of a tracheostomy in form of a forceps according to an embodiment.

Embodiments of the invention are described in more detail below, being illustrated in the attached drawings.

More precisely, a method and device have been developed that make use of all the advantages that percutaneous tracheotomy offers, but which dramatically simplifies and standardizes the technique and eliminates many known risk factors, which the percutaneous technique involves.

The previously known techniques, which are described in the background section, are more difficult to carry out than may be concluded from the above and from what is described in the literature. This applies also for instance to the demonstration CD-Rom and user manual of Cook Critical Care Inc., Bloomington, Ind., which follows with their percutaneous kit.

The different steps, which are performed during the percutaneous tracheotomy, each imply the following issues to be considered:

1. Where should the tracheotomy be made? In the general instructions it is written that it should be made 2 cm above the upper edge of the breastbone. On thick and short necks and with swellings after a long intubation time, it is difficult to find that spot. In Cooks instructions it is recommended that a bronchoscope is introduced through the endotracheal tube and that the incision is made where the light source of the bronchoscope is. However, on a thicker neck it is not possible to identify the light source before an incision is made through the skin. As long as the bronchoscope is inside the endotracheal tube, it is not possible to see a concentrated light source. In order to be able to use the light source in practice as a point of identification, the endotracheal tube firstly has to be pulled up, in such a manner that the tip of the bronchoscope appears outside of the tubes' bottom edge. This necessitates a certain degree of caution in order not to extubate the patient.

In accordance with an embodiment of the present invention, a device similar to a pair of pliers/forceps is used, having a first branch that is designed to be introduced down into the trachea, and a second branch that is located on the outside of the neck, opposite to the first branch. The first branch terminates in a protecting plate, and the other branch is provided with a guiding tube for a tracheal puncturing device, such as an obturator with a sharp tip or a needle. The first branch is introduced down into the trachea through an endotracheal tube.

Embodiments of the device for facilitating tracheotomy are described in more detail further below in this specification.

By means of the forceps like technique, enabled by the embodiment, an inner branch of the device is introduced through the endotracheal tube, while the end of the outer branch during the process indicates the position of the end of the inner branch.

With the conventional tracheotomies, the determination of level becomes highly sensitive, but thanks to the forceps technique according to the embodiment, accuracy becomes less important because one is always positive about being well centered inside the trachea, see the explanation given below, and one always knows that the protection plate of the inner branch will be targeted during the penetration.

If, after all, higher precision is desired concerning how long below the vocal cords the tracheostoma is to be positioned,—which actually is the most important measure in this context, but which previously has not been indicated because the conventional techniques did not offer this possibility—the forceps technique enabled by the embodiment offers the following opportunities:

The inner branch of certain embodiments of the tracheotomy facilitating device may has a scale, e.g. centimeter scale, similar to that found on endotracheal tubes. A reading is made on this scale how far below the end of the tracheal tube the tip of the inner branch or the receiving plate, respectively, is introduced. Thus a measure is provided that facilitates the whole tracheotomy process, as for instance a bronchoscopic surveillance of the process is omittable.

The tracheal tube is pulled up until the cuff meets the lower side of the vocal cords—with other words, the lower end of the endotracheal tube is well below the vocal cords in the trachea.

The distance from the vocal cords is determinable by means of the scale of the inner branch and knowledge about the length of the endotracheal tube, as indicated above.

2. Another difficulty that previously known percutaneous techniques present, is to make the puncture strictly in the centerline of the tracheal wall. Namely, since it may be difficult to find the centerline of patients having a thick neck. When the centerline has been found, after all, it is important to introduce the puncture needle strictly saggital through the wall, both laterally as well as vertically. If this fails, the needle may slide down the side of the trachea and injure vessels, nerves or puncture the lung (pneumothorax) or injure the oesophagus.

This problem is eliminated by means of the forceps technique described herein, as the lower part of the inner branch of the tracheotomy facilitating device always will be arranged in the middle of the trachea as a consequence of it being arranged in the endotracheal tube, which itself is arranged centered in the trachea by means of a cuff. The direction of the tube and, axially of the inner branch, is determined by means of a facemask or the like, which is used for first aid.

The design of the forceps guarantees that the puncture is made correctly with regard to height, due to the angle of the guide at the tip of the outer branch.

3. In case of a puncture created by means of the previously known percutaneous technique, the penetration of the tracheal wall by a needle has to be thoroughly monitored via a bronchoscope, in order to know if one has penetrated the front wall and that the needle shall not travel too deeply and injure the rear wall. A requirement is that both the endotracheal tube and the bronchoscope are pulled up above the puncture site. This requires a certain amount of experience of the person handling the bronchoscope.

Such supervision is not necessary thanks to the tracheotomy technique enabled by the present embodiment, because a sharp object, like an obturator or a needle, and optionally a dilatator, is guided through the tip of the outer branch and is always directed towards a receiving device of the inner branch at a well defined location within the trachea, e.g. facing towards a bowl formed plate of the inner branch after penetration. The sharp object may engage the receiving device or it may be arranged so that it stops at the end of penetration a certain distance from the receiving device. For instance, the tip of the sharp object may be stopped by a suitable seat in the guiding means of the outer branch, e.g. as shown guide 96 in FIG. 9A and guide 86 in FIG. 8. In the case of tracheotomy it is important that the outer wall of the trachea is penetrated in order to create the tracheostoma. However, in certain cases it may be desired to provide a limitation of the stroke of the puncturing device towards the receiving device.

When the dilatator has penetrated the tracheal wall and is put in place, the outer branch may be disconnected. The dilatation of the wall may then be done by means of the dilatator including an introduction of a tracheal port, also called trachport.

An alternative procedure is to introduce the outer branch into the patient down along the side of the endotracheal tube. The branch rests in this case against the front side of the endotracheal tube and will be centered due to the fact that the larynx is triangular with its one apex directed forward.

A further alternative procedure is to arrange the needle in such a way that it penetrates the trachea outwardly from the inside.

Now turning to the embodiments shown in the Figures, an embodiment of a tracheotomy facilitating device according to FIG. 1, comprises a device 1 similar to a pair of forceps 1, having a first branch 14 that is designed to be introduced down into the trachea, and a second branch 12 that is located on the outside of the neck, opposite to the first branch 14. The two branches are pivoted around a common axis 13. The first branch 14 terminates distally in a protecting plate 17, and the other branch is distally provided with a guiding tube 16 for a tracheal puncturing device, such as an obturator or a needle. In use of device 1, the first branch is introduced down into the trachea through an endotracheal tube. This procedure is made easy by two handles 18, 19 on the proximal ends of forceps 1, respectively.

Figure 2:
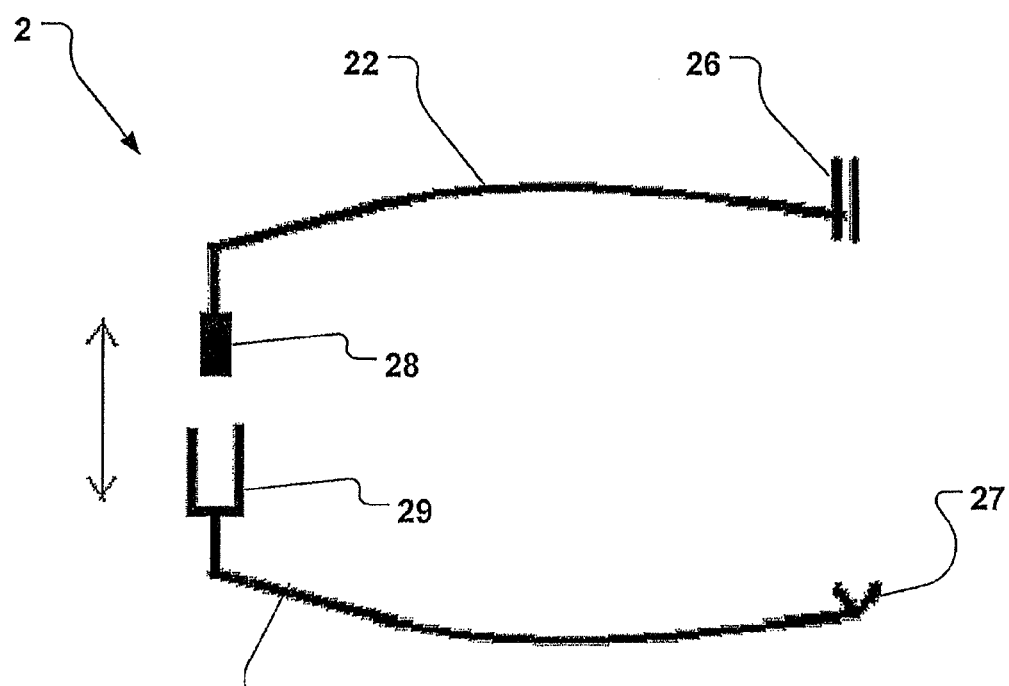
FIG. 2 is a schematic illustration of a device for facilitating tracheotomy in form of two connectable branches according to an embodiment.

A further embodiment of the device is illustrated in FIG. 2. This alternative device comprises two separate branches that cannot move pivotally in relation to each other, but which are pushed into one another at each proximal end 28, 29, respectively, until the opposite ends meet, i.e. the two branches may not be turned laterally. More precisely, this tracheotomy facilitating device 2 comprises a first branch 24 that is designed to be introduced down into the trachea, and a second branch 22 that is located on the outside of the neck, opposite to the first branch 24. The first branch 24 terminates in a protecting plate 27, and the other branch is provided with a guiding tube 26 for a tracheal puncturing device, such as an obturator or a needle. The two branches 22, 24 are connectable to each other at ends 28, 29, as indicated by the double headed arrow in FIG. 2.

Figure 3:
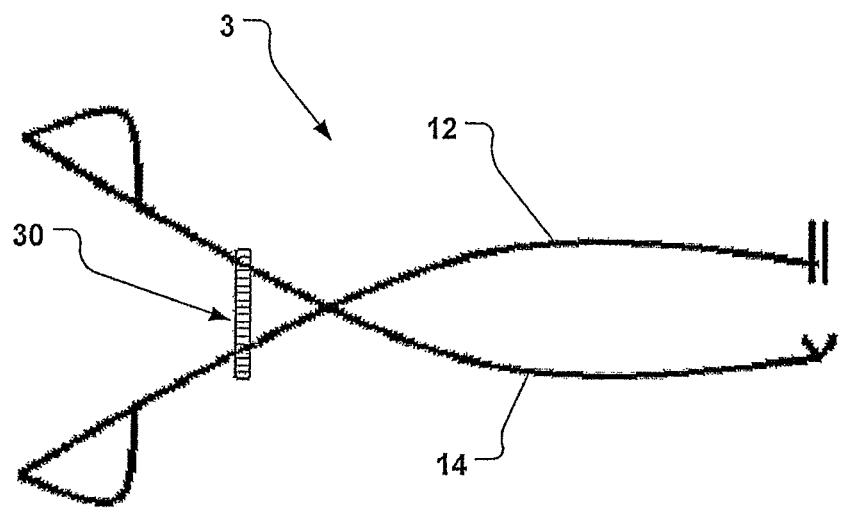
FIG. 3 is a schematic illustration of a device similar to FIG. 1 having a measurement device fastened between its branches according to an embodiment.

Yet another embodiment of the device is illustrated in FIG. 3. This embodiment of a tracheotomy facilitating device 3 is similar to the embodiment shown in FIG. 1, having a first branch 14 and a second branch 12 pivotably connected to each other. However, device 3 further comprises a measurement device 30 in order to provide a determination of the distance from the exterior side of the patients' neck to the inside of the trachea. The measurement device may be a scale fastened between the branches 12, 14, as shown in FIG. 3. By means of the scale a reading is provided how far the distal ends of device 3 are located from each other. Alternative measurement devices comprise magnetic distance indicator units, optical distance measurement units, etc. Moreover, the distance measurement may directly be performed at the tip of the device (not shown in the figures), e.g. by providing a detectable means in the distal end of inner branch 14, such as a magnetic element or another marker detectable from outside the patient's neck, as for instance by magnetic detection (Hall sensor), ultrasonic detector (reflected sound wave), light detector (of suitable tissue penetrating wavelength), etc.

Figure 8:
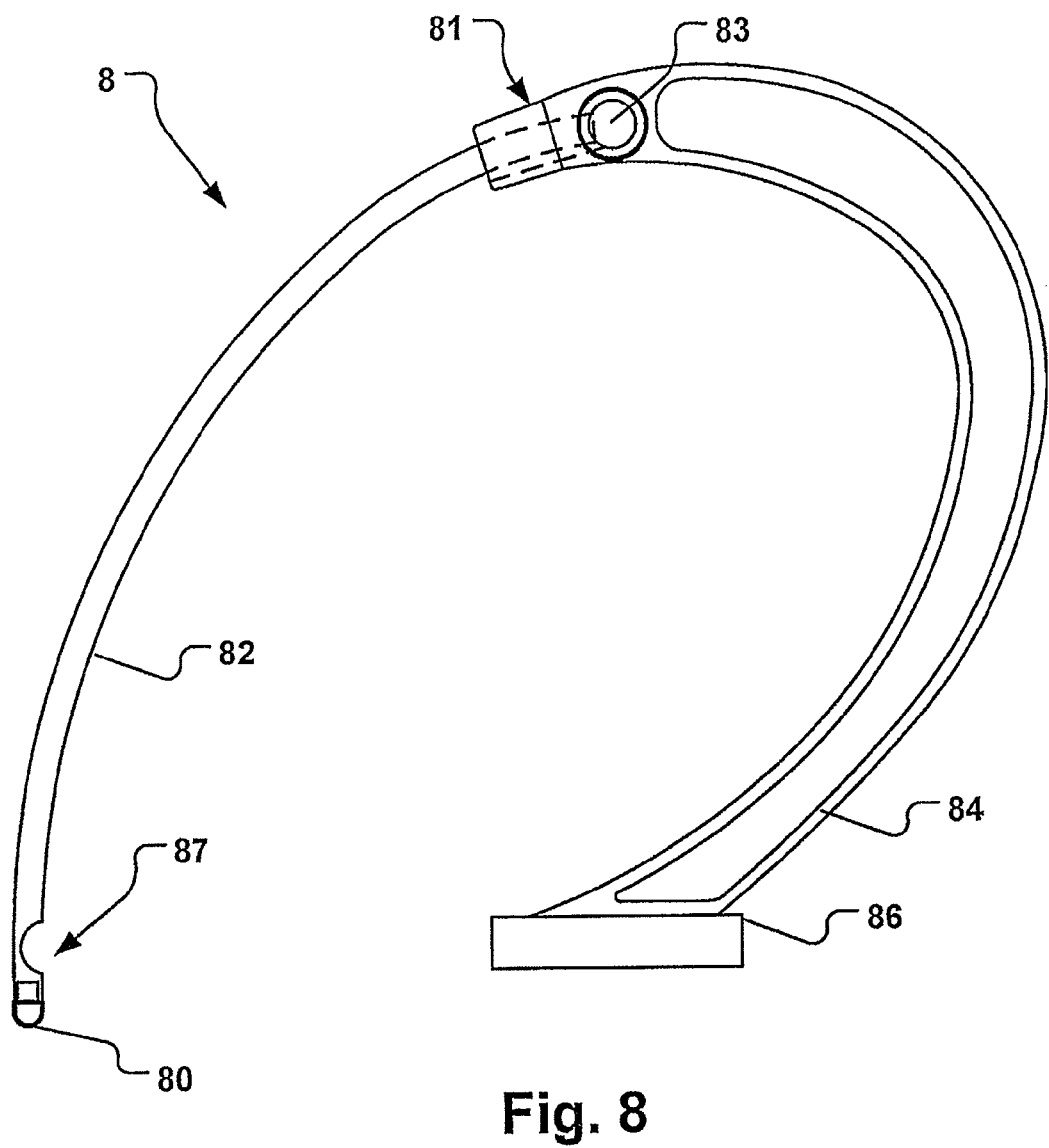
FIG. 8 is a schematic illustration of a further embodiment of a device for facilitating tracheotomy.
Figures 12A, 12B:
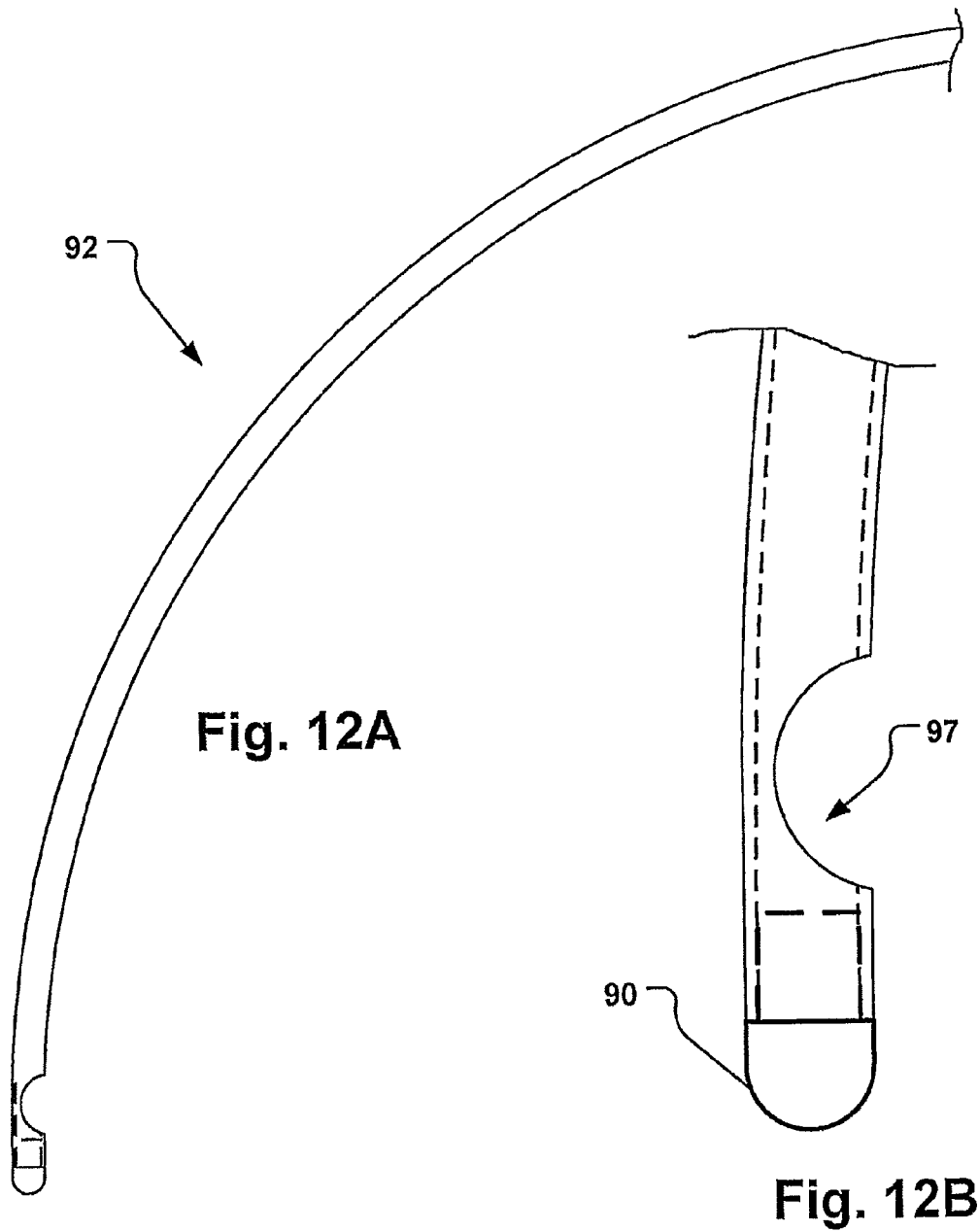
FIGS. 12A and 12B are detailed illustrations of an end region of one of the branches of the device of FIG. 10.

FIG. 8 is a schematic illustration of a further embodiment of a device for facilitating tracheotomy. More precisely, the illustrated device 8 has two branches 82, 84 that are fixed to each other at connection area 81. The inner branch is releasably inserteable into an opening at the proximal end of the outer branch 84, as indicated by the dotted lines in FIG. 8. Thus branch 84 may be fastened to each other, either by sliding the inner branch 82 into the outer branch 84, or by sliding the outer branch 84 over the inner branch 82. This embodiment is similar to the embodiment of FIG. 2 in this regard. Moreover, a suitable locking unit may be provided for locking the two branches to each other in order to avoid unintended release or misalignments. The branches 82, 84 are provided in a curved design further facilitating application of the device 8. Inner branch 82 has an even radius, facilitating introduction down into the trachea or endotracheal tube, as explained below with reference to the exemplary tracheotomy method. Further, inner branch 82 of this embodiment is of circular diameter. Inner branch 82 is hollow in order to allow gas flow there through. The distal tip of inner branch 82 comprises both a receiving device 87 in form of a cutout, as well as a rounded tip 80. Tip 80 may be made of a plastic material having low friction, such as PTFE. This tip region is shown more detailed in FIGS. 12A and 12B.

A gas connector 83 is in fluid communication with the hollow inner of branch 82, leading to receiving device 87.

Figures 9A, 9B:
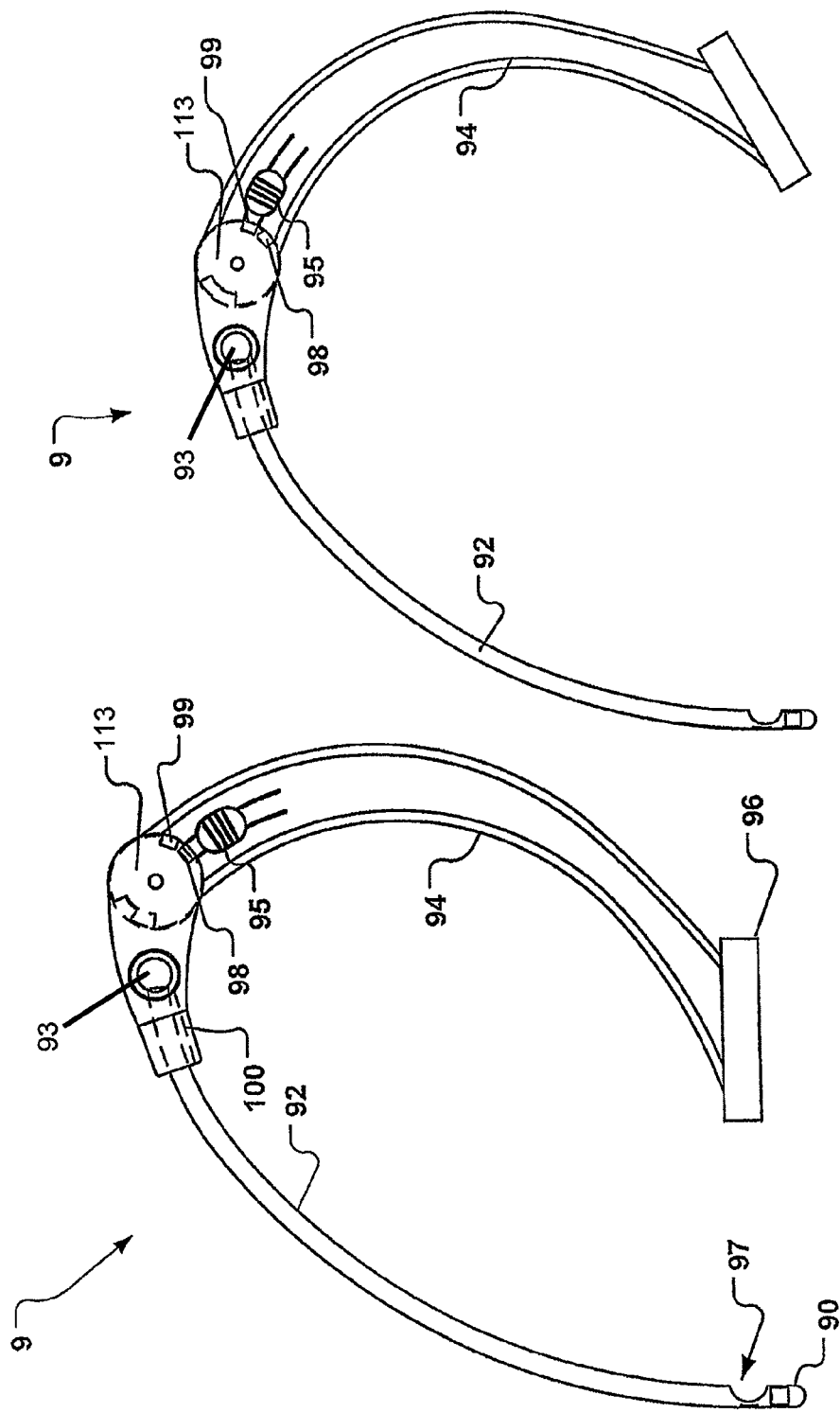
FIGS. 9A and 9B are schematic illustrations of a further device for facilitating tracheotomy in two different states.

FIGS. 9A and 9B are schematic illustrations of a further embodiment of the device for facilitating tracheotomy, wherein two states are illustrated, respectively. FIG. 9A shows the surgical position, whereas FIG. 9B shows the introduction position of device 9. More precisely, the illustrated device 9 has two branches 92, 94 that are pivotable to each other around a joint element 113. The inner branch is inserted into an opening at one proximal end of joint element 113, as shown in FIG. 9A. The branches 92, 94 are provided in a curved design further facilitating application of the device 9, similar as device 8. However, thanks to the possibility to pivot branches 92, 94 relative each other, the use of device 9 made even easier. Inner branch 92 is hollow in order to allow gas flow there through. The distal tip of inner branch 92 comprises both a receiving device 97 in form of a cutout, as well as a rounded tip 90. Tip 90 may be made of a plastic material having low friction, such as PTFE. This tip region is shown more detailed in FIGS. 12A and 12B. A gas connector 93 is in fluid communication with the hollow inner of branch 92, leading to receiving device 97. A Y-piece of a respirator may be connected to gas connector 93 by sliding it onto the latter. Also, gas communication may be provided towards the endotracheal tube from opening by a channel 100, when the tube is surrounding the inner branch 92.

Figures 10A, 10B:
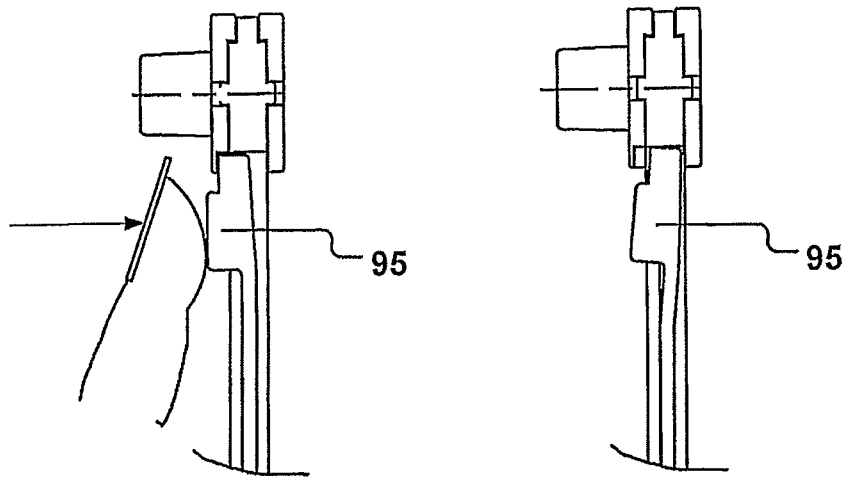
FIGS. 10A and 10B are schematic illustrations illustrating the release of a locking mechanism of the device shown in FIGS. 9A and 9B.

FIGS. 10A and 10B are schematic illustrations illustrating the release of a locking mechanism comprised in joint element 113 of the device 9 shown in FIGS. 9A and 9B. The locking mechanism is based on two notches 98, 99, releasably locking the outer arm 94 to the inner arm 92 in predefined positions. A locking member 95 is engaging one of notches 98, 99 in the surgical and the introduction position of device 9, respectively. FIG. 10A illustrates manual manipulation of locking member 95 by a finger of a user, schematically illustrated on the left of this Figure. The finger presses on member 95, pushing it perpendicular to the outer branch 94. The depressed, unlocked position is shown in FIG. 10B. In this position, the two arms 92, 94 are pivotable relative each other between the locking positions. When releasing pressure on locking member 95 it resiliently returns to the initial position, engaging at its end into one of notches 98, 99, thus providing the desired interlocking.

Figure 11:
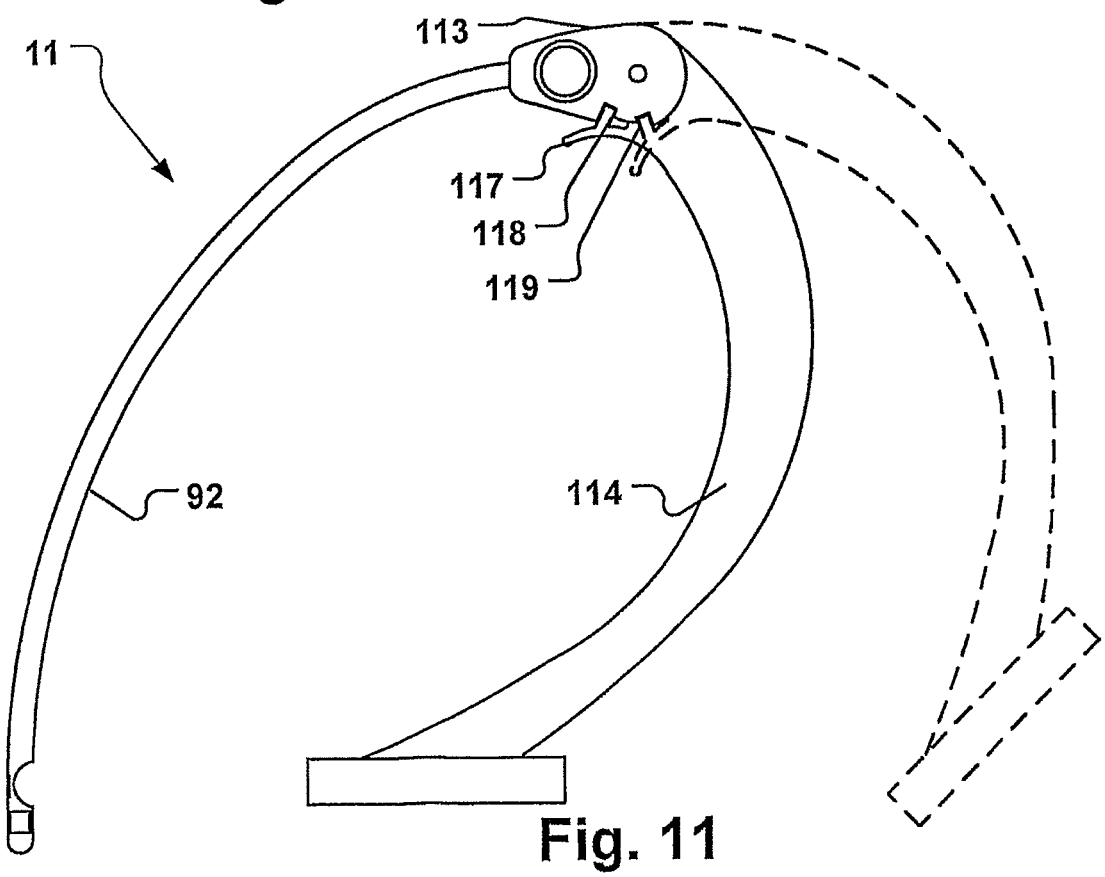
FIG. 11 is a schematic illustration illustrating the two states shown in FIGS. 9A and 9B, respectively, with an alternative locking mechanism.

FIG. 11 is a schematic illustration illustrating the two states shown in FIGS. 9A and 9B, respectively, with an alternative locking mechanism. The device 11 is shown in the surgical position by continuous lines, whereas the introduction position of device 11 is shown in dashed lines. More precisely, the illustrated device 11 has two branches 92, 114 that are pivotable to each other around a joint element 113. The inner branch is inserted into an opening at one proximal end of joint element 113. A locking mechanism comprised in joint element 113 of the device 11 comprises two notches 118, 119 arranged on the periphery of joint element 113, as shown in FIG. 11. Similar to the embodiment of FIGS. 9A and 9B, a locking element 117 is releasably locking the outer arm 114 to the inner arm 92 in predefined positions by engaging one of the notches 118, 119 in the surgical and the introduction position of device 11, respectively. Locking element 117 is released by drawing it out of a notch.

The tracheostomy facilitating device, such as the above illustrated forceps may be made of a particularly rigid plastic material and be disposable, or of metal for multiple use.

Also, the sharp object, such as a needle, scalpel, etc. may be integrated with the distal end region of one of the branches, e.g. be formed as an integral part with said guiding means.

The sharp object is oriented towards the receiving means and travels on a substantially straight trajectory towards said receiving means.

As mentioned above, the inner branch, which is introduced down into the endotracheal tube may have a ventilation channel. Furthermore, the receiving means located at the distal end of this inner branch may be provided in the form of a bowl formed end, eventually integrated into the branch. The other branch, which is outside of the patient, has at its end a guiding means, such as a holder or guide, e.g. of tubular hollow form, for guiding a puncturing means, such as needle, an obturator or another sharp object suitable for penetrating skin and into the trachea for cutting open the desired opening for the tracheostomy in the patient's neck. The guiding means and the receiving means are oriented towards each other, such that for instance when the puncturing means is guided in the guiding means, it is directed towards the receiving means. Alternatively, the puncturing means may for instance be integrated into the guiding means and thus be directed towards the receiving means together with the guiding means, e.g. on a substantially straight trajectory in a single plane. At the end of puncturing, the puncturing means is thus facing the receiving means. The point or line where the branches virtually meet is the place for the tracheotomy.

An exemplary procedure for creating a tracheostomy by tracheotomy, using an embodiment of the device facilitating tracheotomy is given below with reference to FIGS. 4 to 7.

Figure 4:
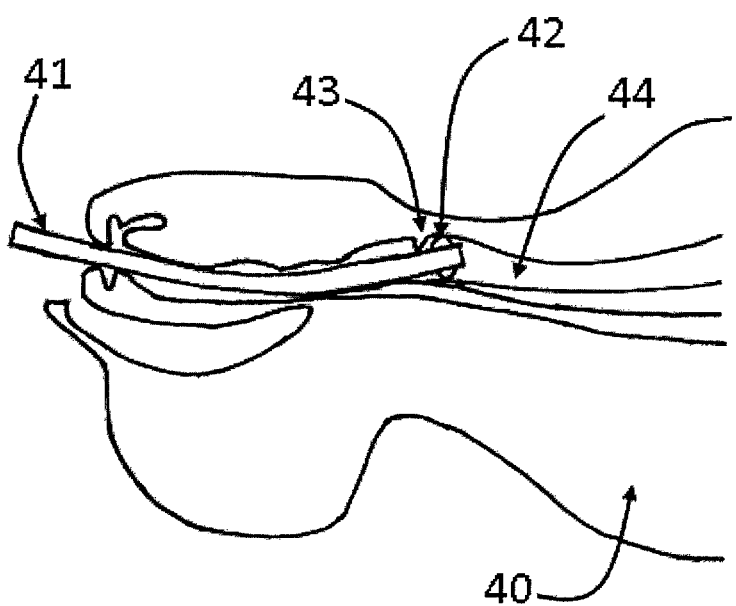
FIGS. 4, 5, 6 and 7 are schematic illustrations of a forceps based tracheotomy.

As shown in FIG. 4, the patient 40 is intubated and ventilated through a traditional endotracheal tube 41 having e.g. a respirator or hand bellows connected at its proximal end for ensuring proper ventilation of the patient during the procedure. The endotracheal tube 41 has a cuff 42, i.e. an inflatable balloon, approximately 1 cm from its distal end. The cuff is positioned below the vocal cords 43, in the trachea 44, see FIG. 4. By inflating the cuff, fixation of the tube 41 in trachea 44, as well as a leak tight, directed respiratory gas flow through it is provided.

The inner branch 14 may be hollow, such that ventilation may be provided through the branch. Alternatively, or in combination, the inner branch may be of a diameter that is smaller than the inner diameter of the endotracheal tube 41, such that it has also a longitudinal measurement rod or measurement scale for providing a control of how far down the branch is in relation to the endotracheal tube.

The cuffed endotracheal tube 41 is then pulled out as far as possible, such that the cuff rests against the lower edge of the vocal cords.

Figure 5:
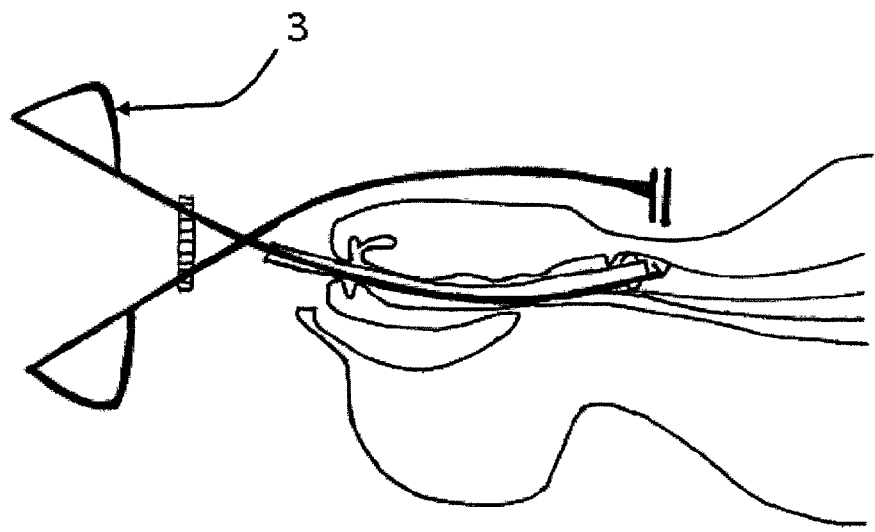
Figure 6:
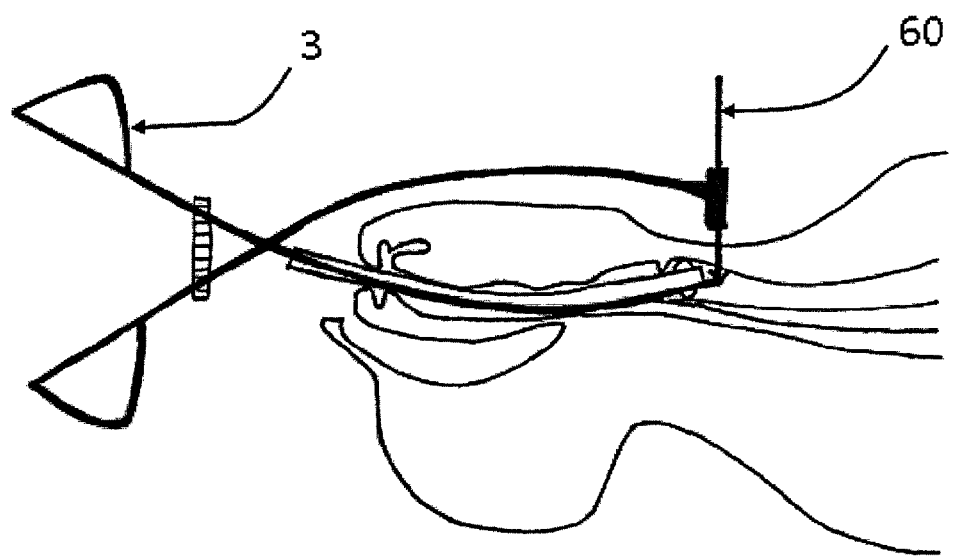
Figure 7:
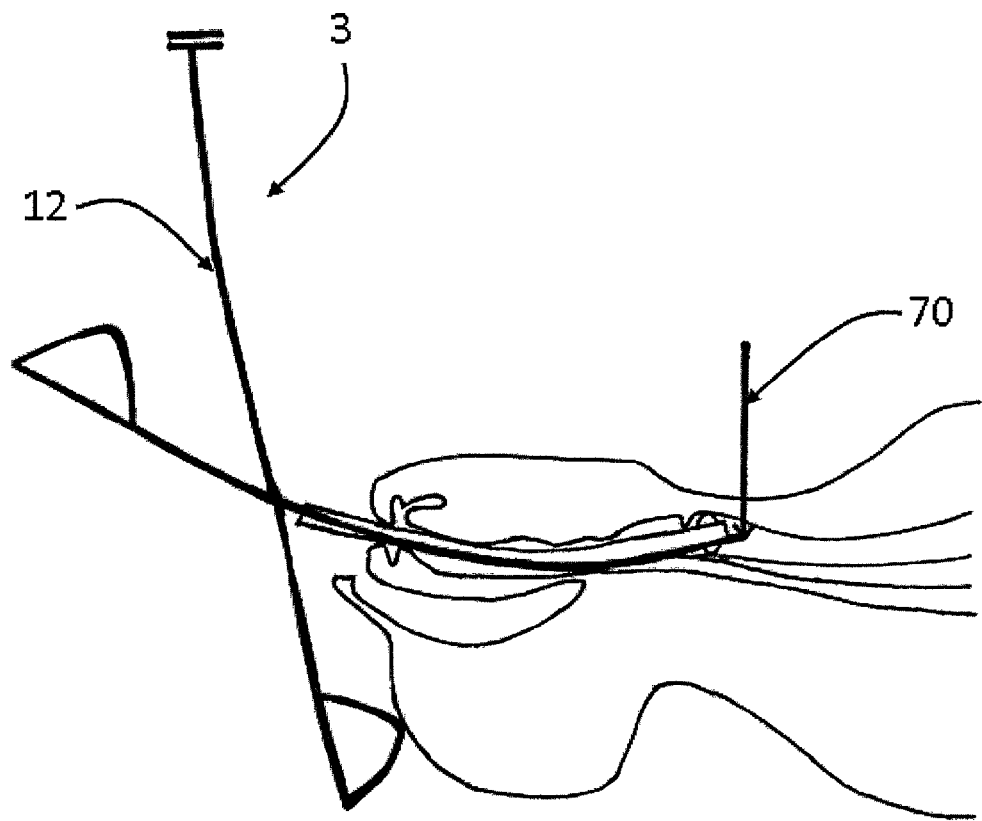

Then the inner branch 14 of device 3 is introduced down the endotracheal tube 41, as is illustrated in FIG. 5.

The connections of the respirator are switched, such that ventilation is provided through the inner branch 14.

The outer branch 12 is moved, i.e. in this case pivoted around axis 13, towards the neck of the patient 40 and the desired position for the tracheotomy—2 cm above the upper edge of the breastbone/or as far below the vocal cords as desired—may be adjusted by moving device accordingly within the endotracheal tube 41 and consequently outside of the neck, respectively, until the desired position is determined.

The guide 16, which is provided in the tip of the outer branch 12, provides guidance of the above mentioned puncturing device, such as a needle 60. Needle 60 is moved towards receiving means 17 through guide 16 for puncturing the trachea. The plate of the inner branch may receive the tip of the needle, such that no risk of injuries of the rear wall of the trachea is run, see FIG. 6. Alternatively, the puncturing device is stopped facing the receiving device, before actually engaging with the receiving device, e.g. by a suitable scale on the puncturing device, or a stop device.

In order to provide a determination of the distance from the exterior side of the patients' neck to the inside of the trachea, a measurement device may be fastened between the branches as shown in FIG. 3.

The outer branch 12 is then fold away/removed in order to facilitate the continued dilatation of the tracheal wall for introduction of a trachport. The trachport will serve as a holder for a conventional tracheal cannula 70, see FIG. 7.

The above description focuses on embodiments of the present invention applicable to facilitating tracheotomy. However, it will be appreciated that the invention is not limited to this application but may be applied to many other applications. The forceps technique may for example even be used in the following cases:

Carrying out a fistula through the tracheaoesophagal wall for laryngectomated patients, both primary as well as secondary, for introduction of a voice valve In connection with laterofixation of paralyzed vocal cords. These pair of forceps will have double guides for lead-through of two needles-one above and one below the vocal cords. A fastening suture may then be conveyed through one of the needles and is then forced inside of the other branch and out through the other needle, and when both branches of the pair of forceps have been removed, the suture may be knot together, resulting in the fixation of the vocal cords.

Although the present invention has been described above with reference to specific embodiments, it is not intended to be limited to the specific form set forth herein. Rather, the invention is limited only by the accompanying claims and, other embodiments than the specific above are equally possible within the scope of these appended claims, e.g. different forms of branches than those described above.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A device for facilitating tracheotomy or carrying out a fistula through the tracheaoesophagal wall, comprising:
   a first branch, adapted to be introduced into the trachea or oesophagus of a patient through the mouth of the patient, such that the distal end thereof is located below the larynx when said first branch is introduced in the trachea, and includes a rounded tip, and
   a second branch, adapted to be arranged at the outside of the neck with the distal end thereof located adjacent to a site that is intended for a tracheostoma or a fistula, wherein
   the first and second branches are curved toward each other from the distal ends of the first and second branches to where the first and second branches are joined, and
   the end of one of the branches comprises a guiding means for a sharp object, and
   the end of the other branch comprises a receiving means, and wherein
   the first branch and the second branch are joined to each other in such a manner that the guiding means is oriented towards the receiving means,
   whereby, when the sharp object penetrates the skin and tracheal wall or tracheaoesophagal wall in order to carry out the tracheostoma or fistula, the sharp object is directed towards the receiving means.

2. The device according to claim 1, further comprising that the first and second branch are joined to each other by means of a join, such that the branches form a device similar to a pair of forceps, a pair of scissors or a pair of tweezers.

3. The device according to claim 2, wherein said first and second branches are movable relative to each other in order to facilitate the introduction of the first branch down the trachea, wherein the branches are moveable relative to each other in a single plane.

4. The device according to claim 1, wherein the second branch is connectable to the first branch after which the first branch is introduced down into the trachea.

5. The device according to claim 1, wherein the first branch is provided with a scale and is arranged to be introduced down an endotracheal tube located in the trachea, such that the scale indicates how far the end of the first branch extends out of the lower end of the endotracheal tube.

6. The device according to claim 5, further comprising a facemask and wherein the endotracheal tube and the first branch are guided by the facemask.

7. The device according to claim 1, wherein the first branch is provided with a through opening for communicating a gaseous medium, such as air, to and/or from the lungs of the patient.

8. The device according to claim 1, wherein the sharp object is a needle, which is adapted to be introduced through said guiding means, which is a tube, and that the receiving means is a bowl shaped plate.

9. The device according to claim 1, wherein the guiding means is constructed to cooperate with the sharp object such that the sharp object stops before engaging with said receiving means.

10. The device according to claim 1, comprising a measurement device for providing a determination of the distance from the exterior side of the patient's neck to the inside of the trachea.

11. The device according to claim 10, wherein said measurement device is a scale indicating the distance between the first and second branches.

12. The device according to claim 1, wherein said guiding means and said sharp object are a single integral formed unit.

13. The device according to claim 1, wherein said sharp object is an integrated part of said distal end of one of said first and second branches.

14. The device according to claim 1, wherein said receiving means is integrated in said first branch.

15. The device according to claim 1, wherein said first branch has a rounded distal end region tip with low friction.

16. The device according to claim 1, wherein at least one of said first and second branches has a smooth outer radius.

17. The device according to claim 1, wherein said first and second branch are releasably or lockably joined by means of a connecting means.

18. The device according to claim 17 wherein said connecting means comprises locking means for at least one of said first and second branch.

19. The device according to claim 18 wherein said locking means is comprised in a joint element.

20. The device according to claim 19 wherein said locking means comprises two notches for releasably locking the first branch to the second branch in predefined positions.

21. The device according to claim 20 said locking means is configured to engage one of said notches at a time in a corresponding operation mode of said device.

22. The device according to claim 1, comprising a gas connector in fluid communication with a hollow inner of the first branch connecting the proximal end of the first branch with an opening at said distal end of said first branch.

23. The device according to claim 22, wherein said hollow inner ends at said receiving means.

24. The device according to claim 22, further comprising a Y-piece connected between said gas connector and a ventilator.

25. The device according to claim 22, further comprising a gas communication channel from said gas connector to an inner of an endotracheal tube that surrounds said first branch, and the proximal end of the endotracheal tube is positioned against an opening of said communication channel remote from said gas connector.

26. The device according to claim 1, wherein said sharp object directed towards receiving means is configured to travel on a substantially straight trajectory towards said receiving means.

27. The device according to claim 1, wherein said device is a single use disposable device.

* * * * *